United States Patent
Magagnoli

(10) Patent No.: US 9,925,363 B2
(45) Date of Patent: Mar. 27, 2018

(54) SPACER DEVICE FOR TREATMENT OF AN INFECTED SEAT OF THE HUMAN BODY

(71) Applicant: Augusto Magagnoli, Bologna (IT)

(72) Inventor: Augusto Magagnoli, Bologna (IT)

(*) Notice: Subject to any disclaimer, the term of this patent is extended or adjusted under 35 U.S.C. 154(b) by 25 days.

(21) Appl. No.: 14/701,343

(22) Filed: Apr. 30, 2015

(65) Prior Publication Data

US 2016/0235955 A1  Aug. 18, 2016

(30) Foreign Application Priority Data

Feb. 16, 2015  (IT) ............... BO2015A0066

(51) Int. Cl.
| | |
|---|---|
| A61M 37/00 | (2006.01) |
| A61F 2/38 | (2006.01) |
| A61F 2/36 | (2006.01) |
| A61B 17/56 | (2006.01) |
| A61F 2/30 | (2006.01) |

(52) U.S. Cl.
CPC ............... *A61M 37/00* (2013.01); *A61F 2/36* (2013.01); *A61F 2/389* (2013.01); *A61F 2/3859* (2013.01); *A61B 2017/561* (2013.01); *A61F 2002/3068* (2013.01); *A61F 2002/30672* (2013.01); *A61F 2002/30677* (2013.01); *A61F 2002/30879* (2013.01); *A61F 2002/30932* (2013.01); *A61F 2002/30937* (2013.01); *A61F 2310/00353* (2013.01); *A61M 2205/04* (2013.01); *A61M 2210/02* (2013.01)

(58) Field of Classification Search
CPC .............................. A61M 31/00; A61M 37/00
USPC ........ 604/48; 623/17.11–17.12, 20.14–23.48
See application file for complete search history.

(56) References Cited

U.S. PATENT DOCUMENTS

| | | |
|---|---|---|
| 5,549,699 A | 8/1996 | MacMahon et al. |
| 6,245,111 B1 | 6/2001 | Shaffner |
| 2007/0016163 A1 | 1/2007 | Santini et al. |
| 2007/0088442 A1* | 4/2007 | Cima ............... A61B 5/055 623/18.11 |
| 2007/0260325 A1* | 11/2007 | Wenz ............... A61L 24/001 623/23.62 |
| 2010/0042213 A1* | 2/2010 | Nebosky ........... A61B 17/56 623/16.11 |

FOREIGN PATENT DOCUMENTS

EP  0025814 A1  4/1981

* cited by examiner

*Primary Examiner* — Yashita Sharma
(74) *Attorney, Agent, or Firm* — Themis Law

(57) ABSTRACT

A temporary disposable spacer device implantable in the human body for treatment of an infected bone seat or a joint seat includes a body provided with at least one coupling surface to the bone seat or joint seat to be treated and recesses along the coupling surface.

13 Claims, 3 Drawing Sheets

SPACER DEVICE FOR TREATMENT OF AN INFECTED SEAT OF THE HUMAN BODY

FIELD OF THE INVENTION

The present invention relates to a spacer device, of the temporary and disposable type, for the treatment of a bone seat or joint seat of a human body suffering from infection.

The present invention also relates to a method of making such a spacer device.

BACKGROUND OF THE INVENTION

It is known that a prosthesis implanted inside a human body can be subject to infection.

When this occurs, the infected prosthesis must be removed from the implantation site and, before implanting another prosthesis, it is necessary for the infection to be eradicated.

During such a step, spacer devices are normally used in order to keep the shape of the bone seat or of the joint seat in which the new prosthesis will be implanted substantially unchanged.

Such a procedure is known as "two-step treatment" for the removal of an infected prosthesis and the implantation of a new prosthesis.

The spacer devices typically used can have a porous outer surface, possibly impregnable with one or more pharmaceutical or medical substances to be released into the human body, at the anatomical area in which their implanting is foreseen.

In such spacer devices the amount of pharmaceutical or medical substance that can possibly be impregnated along the porous outer surface is limited by the depth and by the extension of the surface itself. In this case, the spacer device may not ensure the release of the pharmaceutical or medical substance for a period equal to that necessary for the complete healing of the infected site.

Moreover, in such a spacer device it is difficult to apply, along specific portions thereof, two or more pharmaceutical or medical substances that are different from each other while still keeping such substances separate.

There are also preformed spacer devices that are produced by casting antibiotic-loaded bone cement in a mold until it sets and extracting the set spacer device, which is then processed or finished according to requirements.

Alternatively, the surgeon can make a spacer himself during the operation, using molds, usually made from silicone of suitable geometry, which are filled with antibiotic-loaded bone cement, to which another antibiotic different from the first one is optionally added. Once polymerization has taken place, the surgeon extracts the spacer from the silicone mold, facilitated by the flexible nature of this material, and then proceeds with the implanting, possibly finishing the spacer if necessary.

Also in this case, it is difficult for a surgeon to arrange the pharmaceutical or medical substances in specific portions of the spacer device, since the antibiotic-loaded bone cement cast in the mold arranges itself freely inside it, filling its cavities.

Therefore, there is a need for the surgeon to have a spacer device, in which it is possible to add one or more pharmaceutical or medical substances along specific portions of the device, in a solution that is easy to carry out.

Moreover, there is a need to provide a spacer device that ensures the release of one or more pharmaceutical or medical substances for the entire period required to heal the infected site.

At the same time, these possibilities are associated with the need to have, in any case, a temporary and/or disposable spacer device of predetermined and correct shape and size, without the risk for the surgeon, having to make the spacer device directly in situ, to obtain a shape that is irregular or incompatible with the patient's actual anatomical requirements, or in any case to be finished and processed before implanting.

SUMMARY OF THE INVENTION

The task of the present invention is to improve the state of the art.

In such a technical task, a purpose of the present invention is to provide a spacer device for the treatment of an infected seat of the human body that is easy to use, for releasing at least one pharmaceutical or medical substance in a bone seat or joint seat to be treated.

A further purpose of the present invention is to provide a spacer device for releasing at least one pharmaceutical or medical substance in specific portions of the bone seat or joint seat of the human body with which it is associated, possibly even for long time periods.

Another purpose of the present invention is to provide a spacer device comprising at least one coupling surface configured to promote a stable connection between the spacer device and the bone seat or joint seat with which it is associated.

In accordance with an aspect of the present invention a spacer device is provided as described hereinafter.

Another task of the present invention is a method of making a spacer device as described hereinafter.

The dependent claims relate to preferred and advantageous embodiments of the invention.

BRIEF DESCRIPTION OF THE DRAWINGS

Further characteristics and advantages of the present invention will become clearer from the detailed description of a preferred but not exclusive embodiment of a spacer device, illustrated for exemplary but not limiting purposes in the attached drawings, in which.

DETAILED DESCRIPTION OF EMBODIMENTS OF THE INVENTION

As known, a spacer device is configured to be implanted in a bone seat or joint seat of the human body, typically replacing an infected prosthesis.

A spacer device according to the present invention is of the temporary and/or disposable type.

By the term "temporary" it is meant that, once its function of healing and maintaining the space of the bone seat or joint seat has been carried out, the spacer device will be removed from the area in question and replaced for example with a permanent prosthesis.

In this regard, the spacer device carries out the function of maintaining the joint spaces as well as healing the bone infection by freeing an amount of at least one antibiotic substance in the infected area.

As far as this last aspect is concerned, the spacer manages to heal the infection by releasing an antibiotic in a targeted fashion and in infinitesimal quantity, whereas the application of even high doses of antibiotic, with methods that do not provide for using spacers, like for example washing the infected area with high-dosage antibiotic solutions, does not provide for the same results to be obtained Studies carried out in the field have indeed found that the bone tissue absorbs in a concentrated manner all of the antibiotic molecules (even if they are a few) freed daily by the spacer. This of course happens if the antibiotic is released by the spacer in contact with or adjacent to the bone tissue, in which case the infinitesimal amount of antibiotic locally reaches the effective concentration to eradicate the infection. For this reason it is essential for the spacer to extend for the entire area of the infection, by this meaning that if the infected prosthesis is a long prosthesis then a long spacer will be used and in the case in which the infected prosthesis is short then a short spacer will be used. In the case in which a short spacer is placed where before a long prosthesis was implanted, part of the bone would not be treated with antibiotic, in such a way leaving bacteria free to multiply.

The spacer device according to the invention has a body shaped so as to be able to couple, in a substantially complementary manner, with the bone seat or joint seat to which is must be constrained.

Regarding this, the attached figures illustrate, as an example but not for limiting purposes, some possible configurations of a spacer device according to the present invention.

Figure 1:
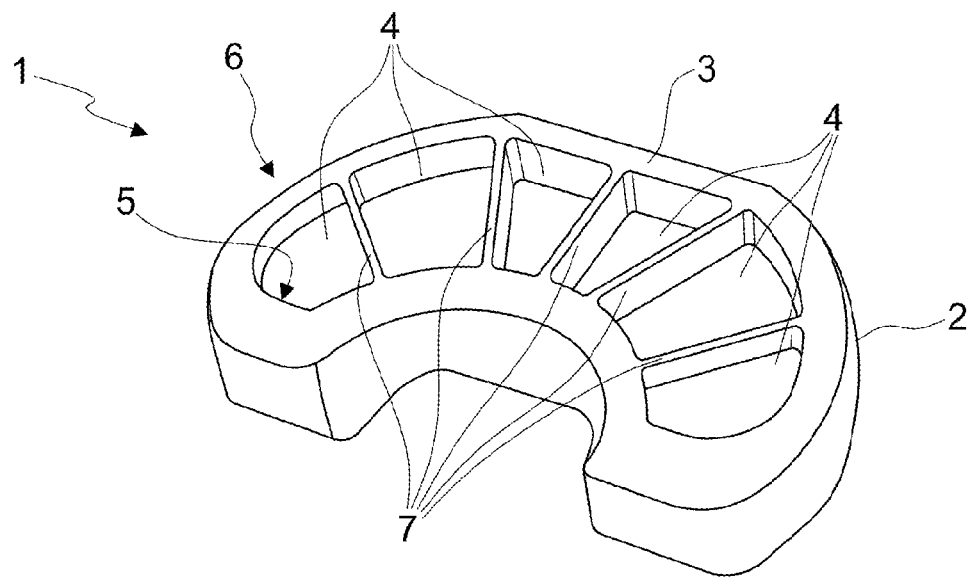
FIG. 1 is a perspective view of the base or lower part of a spacer device according to the present invention.
Figure 2:
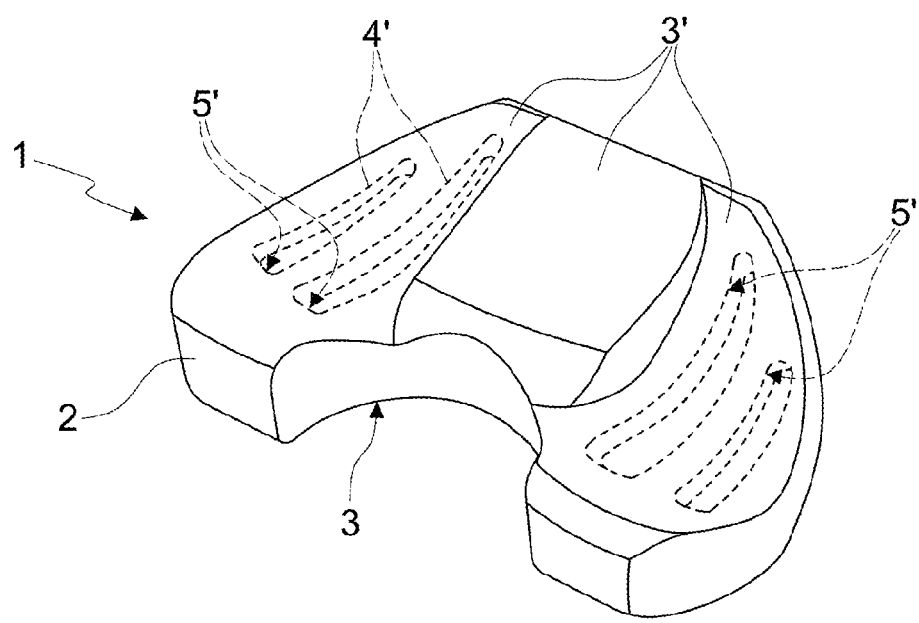
FIG. 2 is a perspective view of the articular or upper part of a spacer device according to FIG. 1.

In greater detail, as an example, FIGS. 1 and 2 illustrate a version of the spacer device according to the present invention shaped to be constrained to the tibial end of a knee joint.

Figure 3:
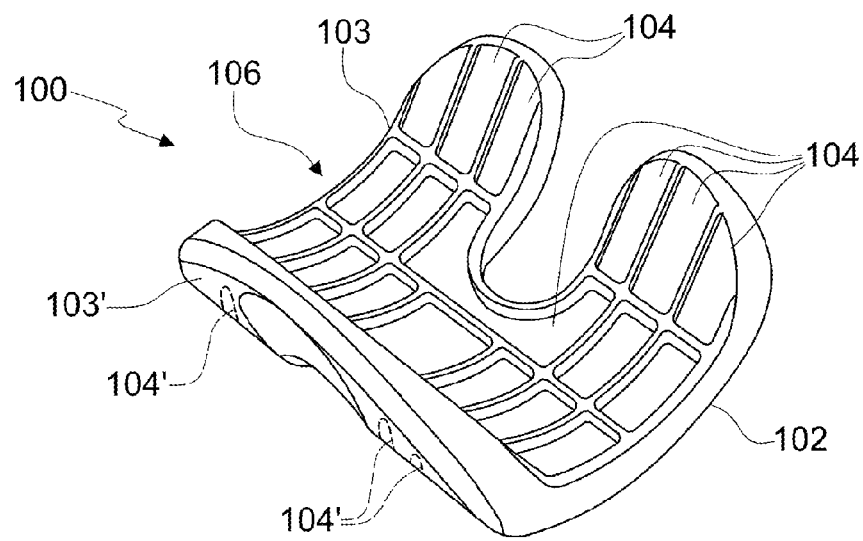
FIG. 3 is a perspective view of the upper part of a further embodiment of a spacer device according to the present invention.
Figure 4:
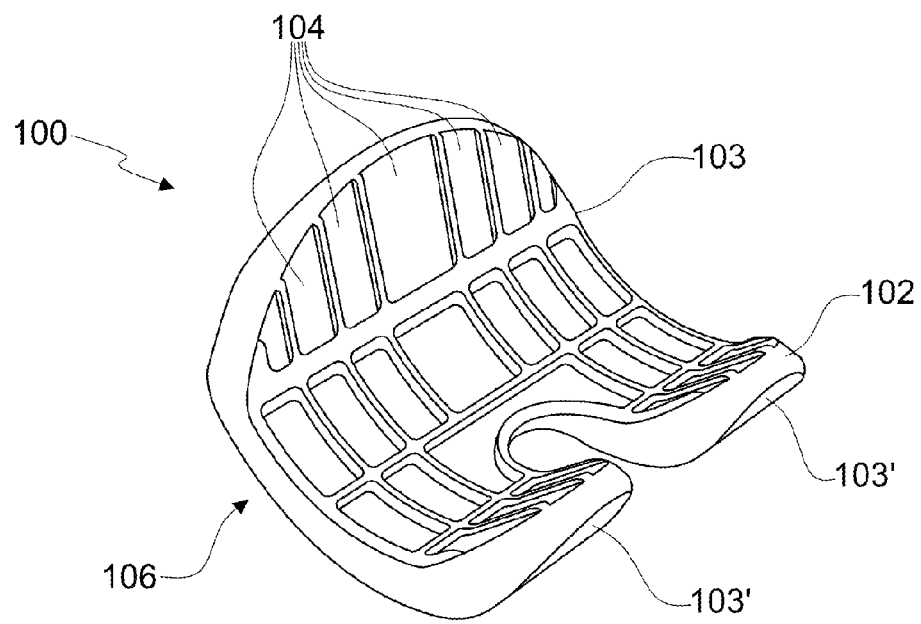
FIG. 4 is a perspective view of the device according to FIG. 3 from to another angle.

A further version of a spacer device according to the present invention is illustrated in FIGS. 3 and 4, in which a spacer device is represented that is foreseen to be associated with the femoral bone end of the knee joint.

Figure 5:
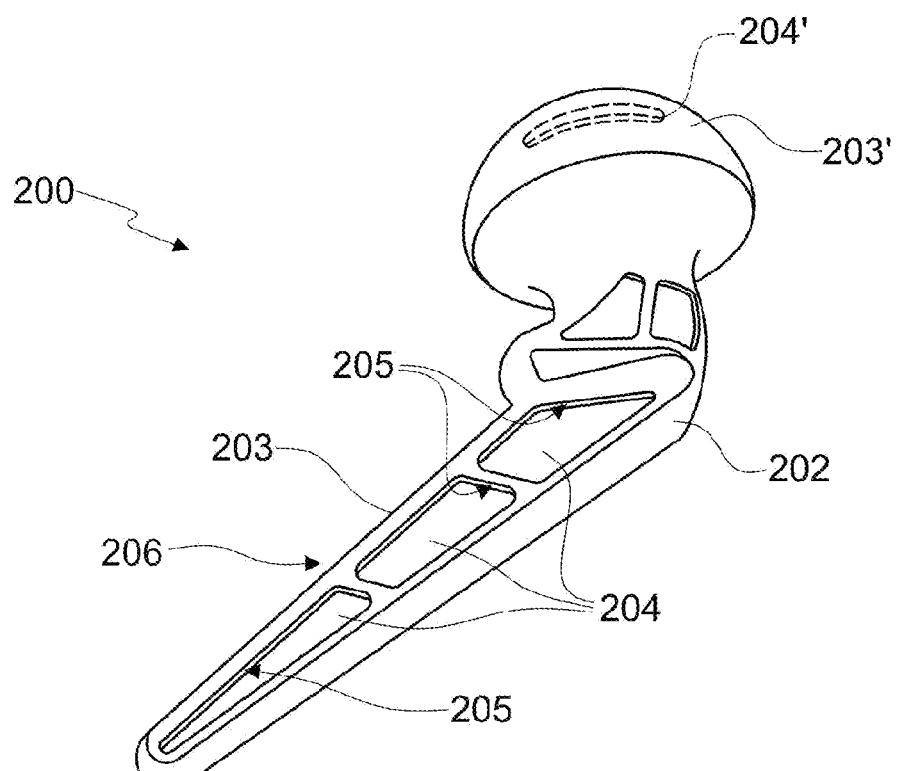
FIG. 5 is a perspective view of the side portion of a further embodiment of a spacer device according to the present invention.

Yet a further version of a spacer device according to the present invention is illustrated in FIG. 5, in which a spacer device for the hip joint is represented, foreseen to be associated with the upper femoral end at the hip joint.

However, further versions of the spacer device according to the present invention are possible, configured differently with respect to what is illustrated in the attached figures, for example for use in the shoulder joint or in the elbow joint or for use in specific sites of the human body, without any limitation.

Hereafter, reference will be made to a spacer device for the tibial end of the knee joint, wholly indicating it with reference numeral 1.

The spacer device 1 comprises a body 2 configured so as to substantially match the bone seat or joint seat with which it must be associated or with part thereof.

The body 2 has at least one surface 3 for coupling the spacer device with the bone seat or joint seat to be treated or with part thereof.

The at least one coupling surface 3 is, therefore, shaped substantially complementary to the bone seat or joint seat to which the spacer device is constrained, in order to promote the correct positioning and connection thereof.

With reference to the embodiment illustrated in FIGS. 1 and 2, the surface 3 is shaped to facilitate the coupling of the body 2 with the tibial end at the knee joint.

The body 2 has at least one recess 4.

In a version of such a spacer device, it has a plurality of recesses 4 positioned along the coupling surface 3.

Figure 6:
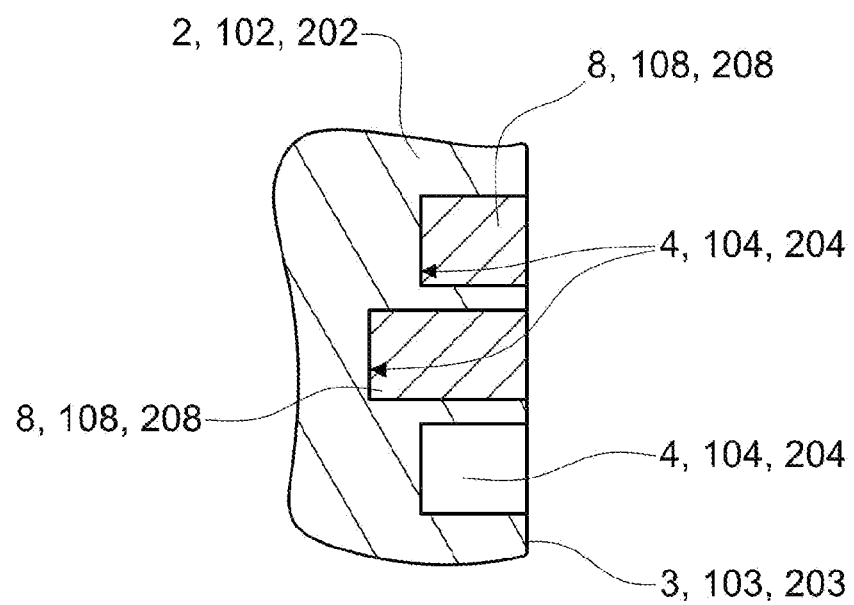
FIG. 6 is a detailed view of a side section of a spacer device according to the present invention, at a coupling surface thereof.

Each recess 4 can extend more or less deeply inside the body 2, as illustrated for example in FIG. 6.

Moreover, the arrangement of the at least one recess 4 or of the plurality of recesses along the coupling surface 3 can vary as a function of specific requirements.

The extension of the recesses 4 can in any case vary as a function of the thickness of the body 2, as described better hereafter.

Each recess 4 determines a corresponding opening 5 through the coupling surface 3.

As described better hereafter, the at least one recess 4 forms a seat for housing a filling material comprising at least one pharmaceutical or medical substance in the body 2 of the spacer device 1.

In a version of the invention, the filling material is applied by the surgeon before implanting the spacer device itself.

According to an aspect of the present invention, the substance to be introduced into the at least one recess 4, or only in some recesses 4 when there are more than one of them, can comprise at least one pharmaceutical or medical substance for treating the infection present in the bone seat or joint seat with which the spacer device 1 is associated.

The recesses 4, in practice, act as stores for storing at least one pharmaceutical or medical substance to be released inside the human body.

The total volume of the recesses 4 or of the recess 4 is thus consistent with the estimated period for the treatment of the infection in the site with which the spacer device is associated.

In fact, a spacer device according to the present invention ensures the release of at least one pharmaceutical or medical substance for the entire estimated period for the treatment of the infection.

The recesses 4 define an open cell structure 6 along the coupling surface 3.

In greater detail, the open cell structure 6 comprises a plurality of cells adjacent to one another, corresponding to the recesses 4.

According to a version, the recesses 4 are adjacent to one another.

The open cells 6 or the recesses 4 are separated from one another by ribs 7 arranged between the recesses 4 themselves or between the cells 6 themselves.

The distance as well as the mutual positioning between the single recesses 4 can vary as a function of the shape of the spacer device 1, and therefore of the shape of its coupling surface 3.

The ribs 7, as well as spacing and separating the recesses 4, act as reinforcing element for the body 2.

Regarding this, the recesses 4 can be made in the body 2 so that the ribs 7 are positioned at the portions of the spacer device 1 that, during use, are subject to greater mechanical stresses, for example wear, flexing, fatigue, etc.

According to a version of the present invention, the body 2 can be made from biologically compatible material, possibly porous.

The biologically compatible material constituting the body 2 can be selected from plastic materials, possibly thermoformable, such as polymethylmethacrylate (PMMA), polyvinylchloride (PVC), polystyrene (PS), polyethylene (PE), ultra high molecular weight polyethylene (UHM-WPE), high or low density polyethylene, etc., or non-polymeric materials, ceramics, metals, metal alloys, organometallic compounds, and/or a combination thereof.

In a version of the present invention, the biologically compatible material is a bone cement based on polymethylmethacrylate (PMMA).

In another version of the invention, the aforementioned biologically compatible material initially has no pharmaceutical or medical substances.

In a further second version, the aforementioned biologically compatible material comprises at least one pharmaceutical or medical substance.

According to a further version of the present invention the biologically compatible material can be a ceramic cement, like for example calcium sulfate known as gypsum or $CaSO_4$, which as well as solidifying in short time periods is able to release calcium ions.

In order to make the body 2, it is nevertheless possible to use further biocompatible materials, with respect to what is described above, without for this reason departing from the scope of protection of the present invention.

According to an aspect of the present invention the at least one recess 4, or overall the plurality of recesses 4, ensure the release of the at least one pharmaceutical or medical substance contained in it/them for a period at least equal to that estimated for the treatment of the infection.

Regarding this, the total volume of the recess(es) 4 to be arranged in a spacer device according to the present invention is calculated as a function of different parameters including the estimated amount of at least one pharmaceutical or medical substance necessary for the aforementioned healing period, the volume of the body 2, the extension of the coupling surface 3, the value of the stresses to which the spacer device is subjected during use, whether or not there are reinforcing cores inside the spacer device itself.

As a general rule, if a spacer device has an ample coupling surface 3 in relation to the volume of the body 2, thus in the presence of a spacer device with low thickness, the at least one recess 4 can have a low depth with respect to their development in plan.

As stated, the shape of the at least one recess 4 can in any case vary and differ from what has been described above, as a function of specific requirements of use.

For example, the single recesses 4 can have different shapes to one another, as a function of the shape of the body 2 and of the coupling surface 3.

As stated, the single recesses 4 can have different depths with respect to the coupling surface 3. Regarding this, FIG. 6 schematically illustrates a detail of a section view of a spacer device, according to the present invention, at the coupling surface 3.

FIG. 6 schematically illustrates, as an example, three recesses 4, arranged adjacent to one another, which extend through the body 2 with different depths, two of which are filled by at least one filling material.

According to a version of the present invention, the recesses 4 can be present along the coupling surface 3, distributed substantially uniformly (see FIGS. 1 and 3).

In this case, the body 2 has an open cell structure 6 spaced apart substantially uniformly along the coupling surface 3.

According to a further version, the recesses 4 may not be uniform along the coupling surface 3.

If the spacer device is foreseen for use in a joint of the human body, it can comprise an articulation surface 3', capable of articulating with a suitable bone seat or with a corresponding surface present in a spacer device of suitable configuration.

With reference to the spacer device 1 illustrated in FIGS. 1 and 2, the articulation surface 3' is opposite the coupling surface 3.

The coupling surface 3 and the articulation surface 3' can be arranged differently to one another, as a function of the shape of the spacer device itself.

The articulation surface 3' can, optionally, have at least one further recess 4'.

The at least one recess 4 or the further recesses 4', similarly to what has been described previously concerning the recesses 4, define an opening 5' or openings 5' through the articulation surface 3'.

The further recesses 4', illustrated with a broken line in FIG. 2, are arranged along the articulation surface 3' aligned along the direction of articulation.

Therefore, the further recesses 4' promote or at least do not hinder the sliding between the articulation surface 3' and the surface of the joint bone seat or of the corresponding spacer device with which the spacer device 1 articulates.

If the joint to which a spacer device 1 according to the present invention must be applied allows a flexing and extension movement between two bone ends about a rotation axis, for example in the case of the knee or elbow joint, the further recesses 4' can be substantially orthogonal to such a rotation axis, and oriented along the flexing-extension direction (see FIG. 2).

The further recesses 4' thus oriented promote or do not hinder the mobility of the joint, since the articulation surface 3' has portions for abutment with the bone end with which it is associated, thus ensuring the mobility of the joint itself.

According to an aspect of the present invention, the spacer device 1 can comprise filling portions or inserts, wholly indicated with reference numeral 8 (see FIG. 6).

The filling portions or inserts 8 act as filling for the recesses 4, 4' present in the body 2.

According to an aspect of the present invention, the filling portions or inserts 8 are made using a filling material of the setting or solidifiable type.

In a version of the invention, the filling material can be prepared by the surgeon during the operation.

Such a filling material can lack pharmaceutical or medical substances and can have them added to it based on the choice of the surgeon and the patient's needs.

In a further version of the invention, the aforementioned filling material can comprise at least one pharmaceutical or medical substance already arranged in the material that constitutes the filling material itself, and possibly it can, in the preparation step, be added to with a further substance.

According to an aspect of the present invention, the filling material, by virtue of the preparation and solidification step to which it is subjected, can be porous.

The size of the pores possibly present in the filling portions or inserts 8 is such as to prevent the occurrence, during use, of bone growth inside them and, therefore, inside the spacer device that comprises them, which as stated is temporary.

One such configuration of the pores, therefore, facilitates the subsequent removal of the spacer device itself from the bone seat or joint seat treated, once its healing function has been carried out.

As an example, the pores can, in one version, have average dimensions of less than 100 microns.

The spacer device 1 is configured so that when, during use, it is implanted in the human body, the filling portions or inserts 8 are in contact with the bone tissues to be treated.

According to a version, the filling portions or inserts 8 are made so as to be flush with the coupling surface 3 and/or with the articulation surface 3'.

According to a further version, the filling portions or inserts 8 are made projecting from the coupling surface 3 and/or from the articulation surface 3'.

According to a further version, some of the filling portions or inserts 8 are formed flush with the coupling surfaces 3, or articulation surfaces 3' and others project from the coupling surfaces 3, or articulation surfaces 3'.

FIGS. 3 and 4 illustrate a further embodiment of a spacer device, wholly indicated with 100, of the type able to be used for the femoral end of the knee joint.

Hereafter, the same components corresponding to those of the embodiment described earlier will be indicated with the same reference numerals increased by one hundred.

The spacer device 100 differs overall from the previous embodiment only for its configuration, since it is foreseen to be associated with the femoral lower end.

The spacer device 100 is suitable for articulating with the spacer device 1.

The spacer device 100 comprises a body 102 that has at least one coupling surface 103 able to be associated with the femoral bone end at the knee joint. The body 102 comprises at least one recess 104 that defines at least one respective opening 105 through the at least one coupling surface 103.

According to an aspect of the present invention, the spacer device 100 can comprise filling portions or inserts, wholly indicated with reference numeral 108 (see FIG. 6), for respective recesses 104.

The volume of the single recesses 104, and consequently of the respective filling portions 108, can vary, amongst other aspects, as a function of the position of the recesses 104 themselves along the at least one coupling surface 103 and of the shape of the body 102.

The spacer device 100 has an articulation surface 103' able to be associated with a tibial abutment portion of the knee joint or with the articulation surface 3 of the spacer device 1. The articulation portion 103' is opposite the at least one coupling surface 103.

The articulation surface 103', optionally, can have further recesses 104', illustrated in FIG. 3 with a broken line, of elongated shape and oriented along the flexing-extension direction of the knee joint.

FIG. 5 illustrates a further embodiment of a spacer device according to the present invention, able to be used in the hip joint, wholly indicated with 200.

Hereafter, the same components corresponding to those of the embodiments described earlier will be indicated with the same reference numerals increased by one hundred.

The spacer device 200 differs from the previous embodiments for the configuration of the body 202, which has a substantially elongated portion or stem, for coupling with the upper femoral end, and a rounded end portion or head, able to be associated with the acetabular cavity and suitable for articulating with it.

At the elongated portion, the body 202 has at least one coupling surface 203, along which recesses 204 are made.

The recesses 204 define respective openings 205 through the at least one coupling surface 203.

As described for the previous embodiments, the at least one coupling surface 203 has an open cell structure 206, in which the cells correspond to the recesses 204.

According to an aspect of the present invention, the spacer device 200 can comprise filling portions or inserts, wholly indicated with reference numeral 208 (see FIG. 6), for at least some of the respective recesses 204.

The recesses 204 can have different depths to each other with respect to the coupling surface 203, as a function of specific requirements.

The body 202 has an articulation surface 203' arranged for articulating with the acetabular seat of the hip joint.

Similarly to what is described for the previous embodiments, the body 202 can comprise a further recess 204' or further recesses 204' arranged along the articulation surface 203'.

As stated, the spacer device 1, 100, 200 according to the present invention comprises a body 2, 102, 202 provided with at least one recess 4, 104, 204 for housing at least one pharmaceutical or medical substance for healing an infection of a bone seat or joint seat of the human body, in which said at least one recess 4, 104, 204 is arranged along at least one coupling surface 3, 103, 203 with the respective bone seat.

The body 2, 102, 202 can also comprise at least one further recess 4', 104', 204' at the articulation surface 3', 103', 203'.

In a version of the invention, the spacer device 1, 100, 200 comprises at least one recess 4, 104, 204 in the coupling surface 3, 103, 203 but it does not comprise any recess in the articulation surface 3', 103', 203'.

The recesses 4, 4', 104, 104', 204, 204' allow a surgeon to arrange at least one pharmaceutical or medical substance or filling portions 8, 108, 208 comprising such at least one substance, which in use are directly in contact with specific portions of the bone tissues to be treated, in specific portions of the spacer device 1, 100, 200, so that it is released in the human body.

The surgeon can decide in which portions of the coupling surface 3, 103, 203 and/or of the articulation surface 3', 103', 203' of the spacer device 1, 100, 200 he can apply at least one pharmaceutical or medical substance.

In particular, the surgeon is helped in this step since the single recesses 4, 4', 104, 104', 204, 204' are independent from each other. Therefore, the at least one substance introduced into them stays confined, during the arrangement of the spacer device for its implanting in the human body, inside the recesses themselves and, therefore, in specific portions of the body 2, 102, 202.

As stated, the total volume of the recesses 4, 4', 104, 104', 204, 204' can vary as a function of various parameters, including the configuration of the spacer device itself and the extension of the coupling surface 3, 103, 203.

Generally, the total volume of the recesses 4, 4', 104, 104', 204, 204' can be comprised between 1%-80%, with respect to the total volume of the body 2, 102, 202.

The highest percentage can be obtained when the material that makes up the body of the spacer device is per sé resistant to loads and to stresses, whilst still being equipped with many recesses (and therefore when the percentage volume occupied by the material of the body is less than the "empty" volume relative to the recesses).

This can occur, for example, in a version of the invention, when the material that constitutes the body of the spacer device is a metal or a material having similar performance in terms of mechanical strength.

Alternatively, the total volume of the recesses 4, 4', 104, 104', 204, 204' can be comprised between 2% and 30% of the total volume of the body 2, 102, 202. Such a percentage—lower than that described earlier—can be used, for example, in a version of the invention, when the body is made from a plastic material, like for example PMMA.

A characteristic of the spacer device according to the present invention is that, although in the presence of a large volume of recesses, they do not alter the final shape of the device itself.

Therefore, the spacer device maintains a predefined or preformed overall shape—even in the presence of the at least one recess—so that the final shape thereof has the advantages of conventional preformed devices.

As stated, indeed, the advantages given by the present invention are associated with the need to have a temporary and/or disposable spacer device having a predetermined and correct shape and size, without the risk of the surgeon, having to carry out the filling of the recesses present in the spacer device directly in situ, being able to obtain a shape that is irregular or incompatible with the actual anatomical or articulation requirements of the patient.

The recesses, indeed, when they are filled with the filling material, recreate the overall or final shape of the spacer device without the need for complicated or further processing by the surgeon, who otherwise would be forced to check that the surfaces created by him with the filling material match the actual anatomical and/or articulation requirements of the patient.

For example, in a version of the invention, the recesses can be filled with the filling material or closed with it in order to define a flat outer surface.

In this regard, the opening or port of such recesses or its outer surface defines a surface that lies substantially on the same plane.

In this case, the surface is flat.

In this case, the opening of the at least one recess or the outer surface of the at least one filling portion or insert is flush with the surface of the body of the spacer device or is flush with the outer edge of the ribs 7, 107, 207.

Consequently, the outer surface of the recess or of the filling portions or inserts 8, 108, 208 that form following the filling of the recesses with the filling material, is flat or not curved.

In this way, when the surgeon fills such recesses, he can flatten the outermost surface of the filling material contained in them even with a spatula, in any case obtaining a definite final overall shape of the spacer device, meeting the anatomical and/or articulation requirements of the patient.

For example, when the at least one recess is positioned in a curved surface of the spacer device, the flat outer surface of the recess or of the at least one filling portion or insert 8, 108, 208, do not interfere with the curved shape of the surface on which they are positioned. Therefore, the outer surface will have dimensions suitable for such a purpose.

The area occupied by the outer surface of the at least one recess or of each recess, in a version of the invention, has values comprised between 10% and 80%, when positioned on a substantially flat surface and/or on an at least partially curved surface of the spacer device in question.

The present invention also concerns a method for making a spacer device 1, 100, 200.

The aforementioned method, initially, foresees to provide a body 2, 102, 202 configured so as to substantially match the bone seat or joint seat with which it must be associated or part thereof.

Thereafter, the method foresees to fill the at least one recess 4, 104, 204 or at least some of the recesses 4, 104, 204 introducing at least one filling material inside them.

If present, the at least one recess 4', 104', 204' or at least some of the further recesses 4', 104', 204' can also be filled with a filling material.

Preferably, such a filling material can comprise at least one pharmaceutical or medical substance.

As stated, typically, the filling material able to be used is of the solidifiable type, like for example bone cement.

After the setting of the filling material in the body 2, 102, 202, filling portions or inserts 8, 108, 208 are formed that, in fact, at the end of solidification form a single body with the body 2, 102, 202 itself.

The spacer device 1, 100, 200 thus formed has a body 2, 102, 202 made up of a first material, and filling portions or inserts 8, 108, 208 made up of at least one second material.

According to a version, the filling material with which the filling portions 8, 108, 208 are made can differ from the material with which the body 2, 102, 202 is made.

In a version, the filling material can comprise at least one first pharmaceutical or medical substance.

According to a further version, the filling material can correspond to that of the body 2, 102, 202.

If, on the other hand, it was selected to use a different material from that of the filling material for the body 2, 102, 202, they could for example have the following combinations.

The body can be obtained by molding of plastic materials through a thermoplastic press.

The plastic materials could be selected from, as stated, PE, UHMWPE, PP, PA, PMMA, PEEK, etc.

The selected plastic material is suitable for being implanted in the human body for a long time.

Alternatively, the body could be made from ceramic molded and fired to vitrification as occurs for medical ceramics like Alumina, Zirconia, etc.

Furthermore, the body could be made from metal or metal alloys with particular antibacterial activity (Silver, etc.) molded for example with MIM technology.

In these cases, the filling material is still bone cement or PMMA.

One of the advantages of such examples is that the material of the containment body is different from steel. Steel, as known, forms a site in which bacteria can nestle and survive. Therefore, a spacer—which is positioned in an infected joint—must not have even minimally exposed parts of steel. If there were, bacteria would quickly settle on the exposed steel surface, said bacteria, possibly protected by their "glycocalyx", could withstand the antibiotic freed from the close spacer device (for example from its shell or body of bone cement).

If, on the other hand, the steel is perfectly embedded in the antibiotic-laden cement, this risk is not present.

The material constituting the body 2, 102, 202 must be resistant to bacteria colonization and this can be achieved, according to an embodiment, by inserting antibiotics or antimicrobials in the thermomolded plastic material or in the ceramic or by using antibacterial metals like, indeed, silver.

The temporary disposable spacer device 1, 100, 200 according to the present invention is ready for use after the setting of the filling material introduced inside the recesses 4, 104, 204.

The at least one pharmaceutical or medical substance present in the filling material can be released gradually, and substantially uniformly, through the at least one coupling surface 3, 103, 203 and/or through the at least one articulation surface 3', 103', 203' of the spacer device 1, 100, 200.

As stated, the recesses act as a reservoir for storing an appropriate reserve of at least one pharmaceutical or medical substance in the body 2, 102, 202 as a function of the estimated period of use of the spacer device 1, 100, 200.

In practice, the spacer device 1, 100, 200 allows the release, through the coupling surface 3, 103, 203 and/or through the at least one articulation surface 3', 103', 203', of at least one pharmaceutical or medical substance during the entire estimated period taken to heal the infection or, possibly, for a longer period.

Moreover, the various recesses are independent from each other, and allow one or more pharmaceutical or medical substances, possibly different from each other, to be stored, keeping them separated in specific portions of the body 2, 102, 202.

The definition given of "porous" element, present in the present description, can be replaced by "semipermeable", without for this reason departing from the scope of protection of the present invention.

According to a further aspect of the present invention, the spacer device 1, 100, 200 can comprise at least one specific diagnostic or measuring device, not illustrated in the figures, housed inside one of the recesses 4, 4', 104, 104', 204, 204'.

As an example, the spacer device 1, 100, 200 could comprise a biomedical/biological microelectromechanical system, such as a bio-sensor, capable of carrying out chemical-physical detections. Such a bio-sensor, which corresponds to a chip, could comprise a miniaturized circuit that in turn includes an accelerometer and/or a thermometer and/or a load cell and/or sensors suitable for detecting further physical magnitudes of a different type.

The chip to be associated inside a spacer device 1, 100, 200 can be selected as a function of specific requirements of use and of the type of detections to be carried out.

By associating such a chip with the spacer device 1, 100, 200 it is thus possible to detect the conditions of use of the spacer device 1, 100, 200, with reference for example to the accelerations and/or to the loads, static or dynamic, to which it is subjected, or to the temperature of the bone seat or joint seat in which it is implanted, etc.

According to a further aspect, the bio-sensor could comprise an integrated interface for transferring the detected data.

As an example, the bio-sensor could comprise data transmission means to allow the detection in real time of the conditions of use of the spacer device 1, 100, 200 with which it is associated, thus allowing the operation of the spacer device 1, 100, 200 to be monitored.

The invention thus conceived can be the subject of numerous modifications and variants, all of which are covered by the inventive concept.

The characteristics described for one version or embodiment can be combined with the characteristics of another version or embodiment, without for this reason departing from the scope of protection of the present invention.

Moreover, all of the details can be replaced with other technically equivalent elements. In practice, the materials used, as well as the contingent shapes and sizes, can be of any type according to requirements without for this reason departing from the scope of protection of the following claims.

The invention claimed is:

1. A spacer device, implantable in a human body for a treatment of a bone seat or a joint seat, comprising:
   a body configured to be coupled to the bone seat or the joint seat of the human body and to provide an articulation surface for a limb, the body comprising,
      a first face and a second face disposed at a distance from one another,
      an outer side wall connecting the first face to the second face;
      a plurality of parallel ribs connecting different points of the outer side wall, the plurality of ribs being reinforcement members of at least a portion of the body against stresses on that portion of the body and defining a plurality of first recesses within the first face,
   wherein each of the first recesses has a closed bottom, an inner side wall, and an open top, and
   wherein said plurality of first recesses is configured to house a filling material.

2. The spacer device according to claim 1, wherein a plurality of second recesses is defined within the second face.

3. The spacer device according to claim 1, wherein a total volume of said first recesses is comprised between 1 and 80%, or between 2% and 30%, or between intermediate percentages between the aforementioned percentage values with respect to a total volume of said body or of said spacer device.

4. The spacer device according to claim 1, wherein said body further comprises one or more filling portions or inserts comprising said filling material, for filling at least one of said first recesses.

5. The spacer device according to claim 4, wherein said one or more filling portions or inserts have pores.

6. The spacer device according to claim 4, wherein said filling material in at least one of said filling portions or inserts comprises at least one first pharmaceutical or medical substance, and wherein said filling material in at least one other of said filling portions or inserts comprises a second pharmaceutical or medical substance different from said first pharmaceutical or medical substance.

7. The spacer device according to claim 4, wherein at least one of said filling portions or inserts is flush with said first face, or wherein at least one of said filling portions or inserts has an opening, or a flat or planar outer surface.

8. The spacer device according to claim 4, wherein at least one of said filling portions or inserts projects outwardly of said first face.

9. The spacer device according to claim 1, wherein said filling material is of a setting or solidifiable type.

10. The spacer device according to claim 6, wherein said pharmaceutical or medical substance is an antibiotic.

11. The spacer device according to claim 1, wherein said spacer device has pores.

12. The spacer device according to claim 1, wherein said articulation surface is configured to articulate with a bone seat or joint seat or with a corresponding surface provided in a spacer device of mating configuration.

13. The spacer device according to claim 12, wherein said articulation surface has at least one recess defining an opening along said articulation surface, or wherein said articulation surface has at least one recess defining an opening having an outer surface or port that is flat, planar, or flush with said articulation surface.

* * * * *